United States Patent
Wu (10) Patent No.: US 9,429,504 B2
(45) Date of Patent: Aug. 30, 2016

(54) TESTING TOOL AND TESTING METHOD THEREOF

(71) Applicant: Wistron Corporation, New Taipei (TW)

(72) Inventor: Congfa Wu, New Taipei (TW)

(73) Assignee: Wistron Corporation, New Taipei (TW)

(*) Notice: Subject to any disclaimer, the term of this patent is extended or adjusted under 35 U.S.C. 154(b) by 402 days.

(21) Appl. No.: 13/974,052

(22) Filed: Aug. 23, 2013

(65) Prior Publication Data

US 2014/0360280 A1 Dec. 11, 2014

(30) Foreign Application Priority Data

Jun. 6, 2013 (CN) .......................... 2013 1 0224749

(51) Int. Cl.
*G01N 3/20* (2006.01)
*G01M 99/00* (2011.01)

(52) U.S. Cl.
CPC .............. *G01N 3/20* (2013.01); *G01M 99/007* (2013.01)

(58) Field of Classification Search
CPC ....... G01N 3/20; G01N 23/225; G01R 1/073
USPC .......................................................... 73/763
See application file for complete search history.

(56) References Cited

U.S. PATENT DOCUMENTS 5,378,982 A * 1/1995 Feigenbaum .......... G09G 3/006
324/756.02
6,516,655 B1 * 2/2003 Adrian ..................... G01N 3/42
73/760
6,765,203 B1 * 7/2004 Abel .................. G01N 23/2251
250/305
2012/0268882 A1 10/2012 McClure

FOREIGN PATENT DOCUMENTS

| CN | 2541940 Y | 3/2003 |
|---|---|---|
| TW | 497718 | 8/2002 |
| TW | 497718 U | 8/2002 |
| TW | 200426373 | 12/2004 |

(Continued)

OTHER PUBLICATIONS

Office action mailed on Oct. 6, 2014 for the Taiwan application No. 102122559, filing date: Jun. 25, 2013, p. 1 line 10~14, p. 2~6 and p. 7 line 1~9.

(Continued)

*Primary Examiner* — Lisa Caputo
*Assistant Examiner* — Octavia Hollington
(74) *Attorney, Agent, or Firm* — Winston Hsu; Scott Margo (57) ABSTRACT

A testing tool includes a tool body, a panel imitation member disposed on the tool body, an indicating device, and a probe device. A test panel cover is detachably disposed on the tool body. The probe device is disposed in the panel imitation member and includes a probe and a conductive member disposed under the probe. The probe is elastically disposed through the panel imitation member between initial and triggering positions. When the probe is located at the initial position, the probe extends out from the panel imitation member to abut against the test panel cover. When the test panel cover is sunken inward to contact with the panel imitation member so as to drive the probe to the triggering position, the probe contacts with the conductive member to electrically conduct the indicating device.

18 Claims, 9 Drawing Sheets

(56) References Cited

FOREIGN PATENT DOCUMENTS

| | | |
|---|---|---|
| TW | I249036 | 2/2006 |
| TW | 200928374 | 7/2009 |

OTHER PUBLICATIONS

Office action mailed/issued on Jun. 3, 2016 for CN application No. 201310224749.X, p. 3 line 5-30, pp. 4-5 and p. 6 line 1-2.

* cited by examiner

TESTING TOOL AND TESTING METHOD THEREOF

BACKGROUND OF THE INVENTION

1. Field of the Invention

The present invention relates to a testing tool and a testing method thereof, and more specifically, to a testing tool for testing inward deformation of a test panel cover and a testing method thereof.

2. Description of the Prior Art

With development of the metal forming process, a metal casing has been widely applied to a conventional portable electronic apparatus (e.g. a notebook) for further improving the appearance quality of the portable electronic apparatus. One of the most representative examples is that a panel cover for covering a liquid crystal panel on a notebook is manufactured by a metal (e.g. aluminum) connection process.

However, during the manufacturing process of a metal panel cover, a residual stress could be formed at a position on the metal panel cover where a surface treatment is performed. For example, an aluminum panel cover usually has a residual stress formed therein after a punching process for forming a trademark and a surface milling process are sequentially performed. As a result, when a user presses the aluminum panel cover at a position where a surface treatment is performed (e.g. a position where the trademark is formed), the residual stress could cause the aluminum panel cover to be sunken inward and then generate sound like a drumbeat. That is to say, if the aluminum panel cover has an excessive residual stress formed therein and is then assembled with a portable electronic apparatus for covering a liquid crystal panel of the portable electronic apparatus, the excessive residual stress could cause the aluminum panel cover to be sunken inward so as to collide with the liquid crystal panel when the aluminum panel cover is pressed. Accordingly, the aluminum panel cover may damage the liquid crystal panel to cause a moire problem or a hotspot problem, so that the display quality of the liquid crystal panel could be influenced greatly.

SUMMARY OF THE INVENTION

An objective of the present invention is to provide a testing tool for testing inward deformation of a test panel cover and a testing method thereof to solve the aforesaid problem.

The present invention provides a testing tool for testing inward deformation of a test panel cover. The testing tool includes a tool body, a panel imitation member, an indicating device, and a probe device. The test panel cover is detachably disposed on the tool body. The panel imitation member is disposed on the tool body. The panel imitation member is contained between the tool body and the test panel cover when the test panel cover is disposed on the tool body. The indicating device is disposed on the tool body. The probe device is disposed in the panel imitation member. The probe device includes a probe and a conductive member. The probe is elastically disposed through the panel imitation member between an initial position and a triggering position and coupled to the indicating device. The probe extends out from the panel imitation member to abut against the test panel cover when the probe is located at the initial position. The conductive member is disposed under the probe and coupled to the indicating device. The probe contacts with the conductive member to electrically conduct the indicating device when the test panel cover is sunken inward to contact with the panel imitation member so as to drive the probe to the triggering position.

According to the claimed invention, a limiting block protrudes outwardly from the probe and the probe device further includes a first elastic member. The first elastic member is mounted on the probe and disposed between the limiting block and the conductive member for providing elastic force to drive the probe to the initial position.

According to the claimed invention, the probe device further includes an insulation member. The insulation member is mounted on the probe. Two ends of the first elastic member abut against the limiting block and the insulation member.

According to the claimed invention, the testing tool further includes at least one sliding block and at least one hook. The sliding block is movably disposed in the tool body between a releasing position and an engaging position. The hook is disposed on the sliding block for hooking the test panel cover to position the test panel cover on the tool body when the test panel cover is disposed on the tool body and the sliding block moves to the engaging position. The hook is further used for being separate from the test panel cover when the sliding block moves to the releasing position.

According to the claimed invention, the test panel cover has at least one engaging slot. The hook is disposed on the sliding block corresponding to the engaging slot. The hook is engaged with the engaging slot to position the test panel cover on the tool body when the test panel cover is disposed on the tool body and the sliding block moves to the engaging position. The hook is separate from the engaging slot when the sliding block moves to the releasing position.

According to the claimed invention, the testing tool further includes at least one second elastic member disposed between the sliding block and the tool body for providing elastic force to drive the sliding block to the engaging position.

According to the claimed invention, the testing tool further includes a driving device disposed in the tool body and connected to the sliding block for driving the sliding block to the releasing position.

According to the claimed invention, the driving device includes at least one air pressure rod and a switch. The air pressure rod is connected to the sliding block. The switch is disposed on the air pressure rod for controlling the air pressure rod to drive the sliding block to the releasing position.

The present invention further provides a testing method for utilizing a testing tool to test inward deformation of a test panel cover. The testing tool includes a tool body, a panel imitation member, an indicating device, and a probe device. The panel imitation member is disposed on the tool body. The probe device includes a probe and a conductive member. The probe is movable up and down relative to the panel imitation member and coupled to the indicating device. The conductive member is coupled to the indicating device. The testing method includes disposing the test panel cover on the tool body to abut against the probe, pressing the test panel cover to make the test panel cover sunken inward relative to the panel imitation member so as to drive the probe to move downward relative to the panel imitation member, and determining whether the test panel cover has been sunken inward to contact with the panel imitation member according to a testing result of whether the probe moves downward to contact with the conductive member so as to electrically conduct the indicating device.

According to the claimed invention, the testing tool further includes at least one hook and the step of disposing the test panel cover on the tool body to abut against the probe includes utilizing the hook to be detachably engaged with the test panel cover for positioning the test panel cover on the tool body.

According to the claimed invention, the step of utilizing the hook to be detachably engaged with the test panel cover for positioning the test panel cover on the tool body includes pneumatically driving the hook to be separate from the test panel cover.

According to the claimed invention, the indicating device is an indicating lamp and the indicating device emits light to indicate that the test panel cover has been sunken inward to contact with the panel imitation member.

In summary, the testing tool provided by the present invention adopts the testing method of determining whether the test panel cover is sunken inward to drive the probe to electrically conduct the indicating device, for helping the user determine whether the test panel cover has a risk to damage the liquid crystal panel. In such a manner, via the aforesaid testing method, the user could accurately determine whether to perform a structural enhancement (e.g. a structural strengthening process or a stress relief process) process on the test panel cover or directly assemble the test panel cover with the liquid crystal panel. Thus, the present invention could efficiently prevent the aforesaid prior art problem (e.g. moire or hotspot) caused by the panel cover with an excessive residual stress damaging the liquid crystal panel, so as to improve the display quality of the liquid crystal panel.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
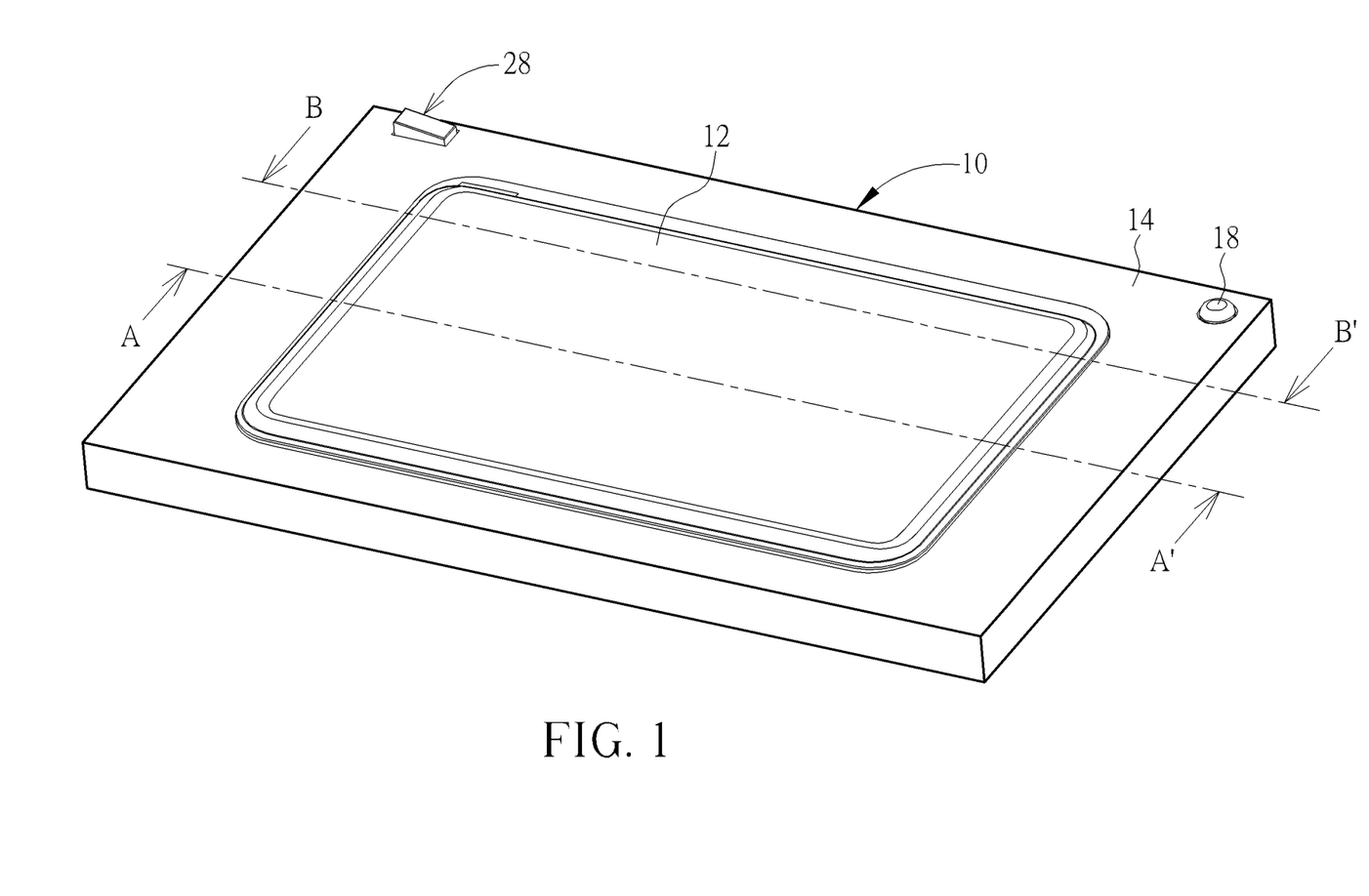
FIG. 1 is a diagram of a test panel cover being disposed on a testing tool according to an embodiment of the present invention.
Figure 2:
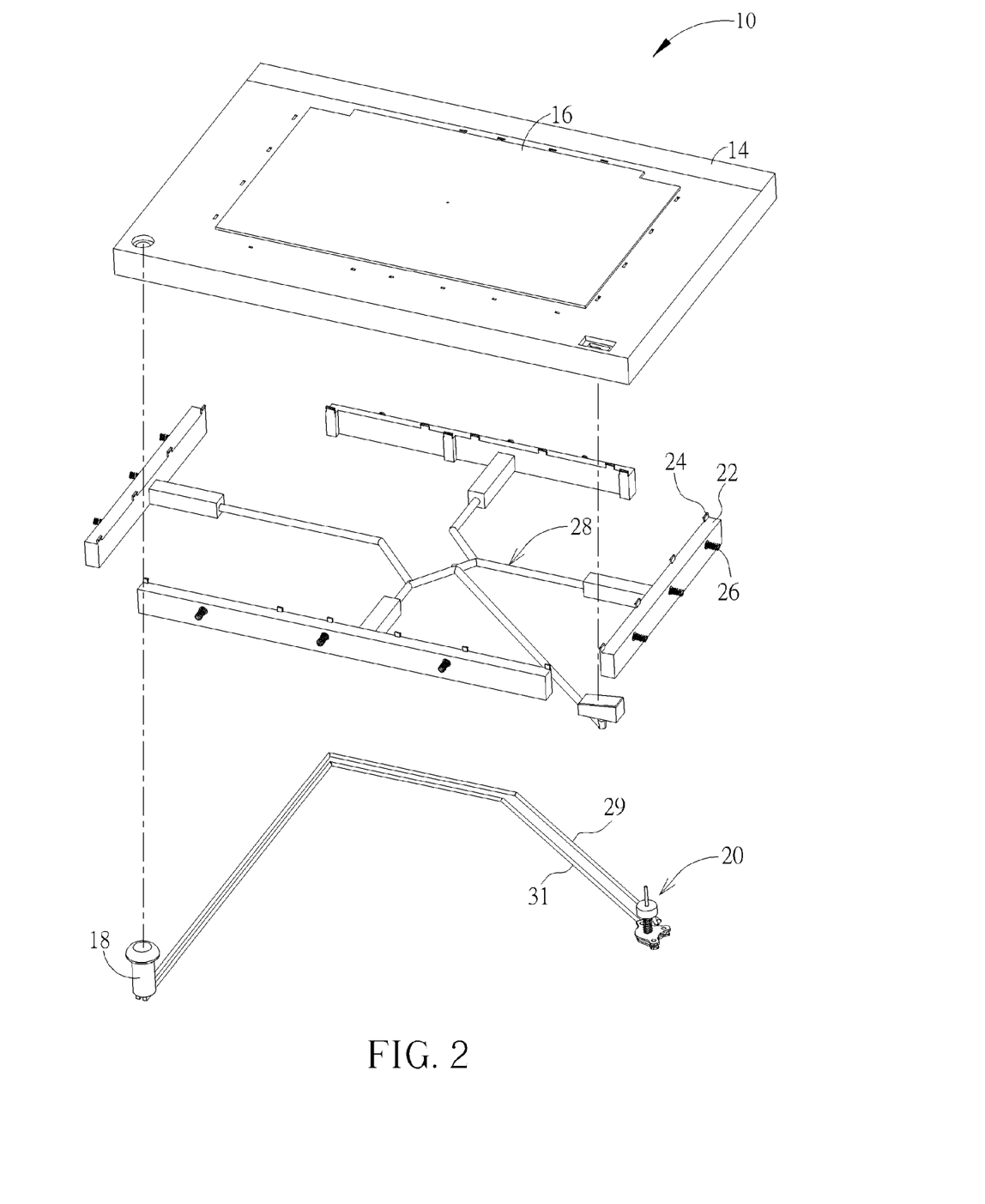
FIG. 2 is an exploded diagram of the testing tool in FIG. 1.

Please refer to FIG. 1 and FIG. 2. FIG. 1 is a diagram of a test panel cover 12 being disposed on a testing tool 10 according to an embodiment of the present invention. FIG. 2 is an exploded diagram of the testing tool 10 in FIG. 1. The test panel cover 12 could be a back cover for containing a liquid crystal panel of a portable electronic apparatus cooperatively with a panel bezel. The testing tool 10 is used for testing inward deformation of the test panel cover 12 so as to help a user determine whether the test panel cover 12 has a risk to damage the liquid crystal panel. As shown in FIG. 1 and FIG. 2, the testing tool 10 includes a tool body 14, a panel imitation member 16, an indicating device 18, a probe device 20, at least one sliding block 22, at least one hook 24, at least one elastic member 26, and a driving device 28. The test panel cover 12 is detachably disposed on the tool body 14. The panel imitation member 16 could be an imitation workpiece having the same size as a liquid crystal panel suitable for the test panel cover 12. The panel imitation member 16 is disposed on the tool body 14, meaning that the panel imitation member 16 could be contained between the tool body 14 and the test panel cover 12 when the test panel cover 12 is disposed on the tool body 14. The indicating device 18 is disposed on the tool body 14. In this embodiment, the indicating device 18 could be preferably an indicating lamp (e.g. a light emitting diode) for emitting light to let the user clearly know the testing result of the testing tool 10, but not limited thereto, meaning that the indicating device 18 could be other conventional indicating apparatus instead. For example, in other embodiment, the indicating device 18 could be a speaker for generating sound to let the user know the testing result of the testing tool 10.

Figure 3:
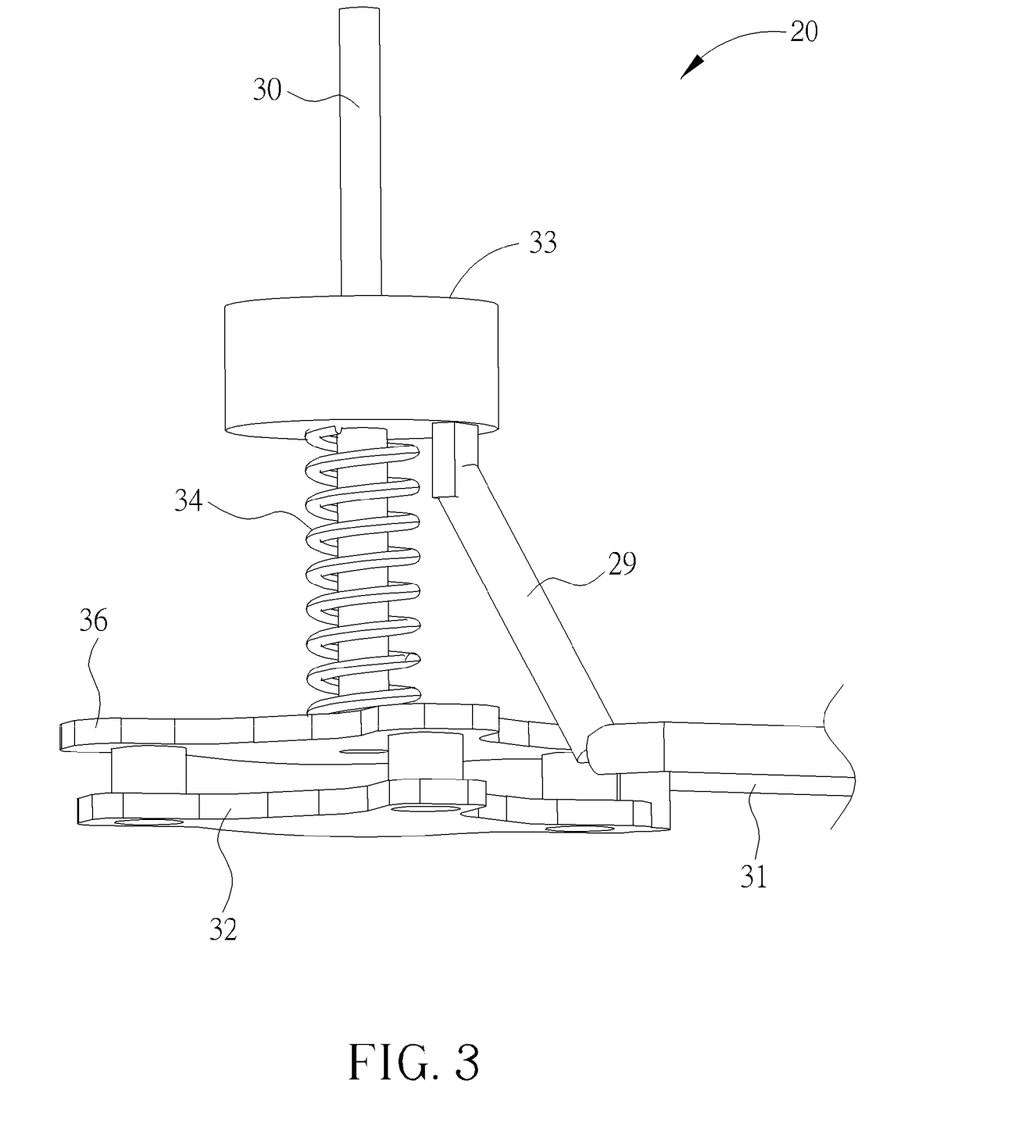
FIG. 3 is a partial enlarged diagram of a probe device in FIG. 2.

Please refer to FIG. 2 and FIG. 3. FIG. 3 is a partial enlarged diagram of the probe device 20 in FIG. 2. As shown in FIG. 2 and FIG. 3, the probe device 20 is disposed in the panel imitation member 16 and includes a probe 30 and a conductive member 32. The probe 30 is disposed through the panel imitation member 16 and is elastically movable relative to the panel imitation member 16. The conductive member 32 could be preferably a conductive sheet (e.g. a brass sheet). The conductive member 32 is disposed under the probe 30. In this embodiment, the probe 30 is coupled to the indicating device 18 via a cable 29 as shown in FIG. 2, and the conductive member 32 is coupled to the indicating device 18 via a cable 31 as shown in FIG. 2. That is, before the probe 30 has not contacted with the conductive member 32 yet (as shown in FIG. 3), the probe 30 and the conductive member 32 could cause the indicating device 18 to be in an open circuit state so that the indicating device 18 is unable to emit light. On the contrary, after the probe 30 has contacted with the conductive member 32, the probe 30 and the conductive member 32 could electrically conduct the indicating device 18 so that the indicating device 18 could emit light. In such a manner, whether the probe 30 contacts with the conductive member 32 could be determined by whether the indicating device 18 emits light or not. As for the related description for the elastic motion design of the probe 30 and the insulation design between the probe 30 and the conductive member 32, it is provided as follows.

In this embodiment, as shown in FIG. 3, a limiting block 33 could protrude outwardly from the probe 30 and the probe device 20 could further include an elastic member 34 and an insulation member 36. The elastic member 34 could be preferably a spring. The elastic member 34 is mounted on the probe 30 and two ends of the elastic member 34 abut against the limiting block 33 and the insulation member 36 respectively. The insulation member 36 is mounted on the probe 30 to separate the probe 30 from the conductive member 32. In such a manner, via the aforesaid designs, the elastic member 34 could provide elastic force for driving the probe 30 to return its original position, and the testing tool 10 could utilize the insulation member 36 to prevent the probe 30 from accidentally contacting with the conductive member 32. To be noted, the elastic motion design of the probe 30 could be not limited to the aforesaid embodiment. That is, the testing tool 10 could also adopt other elastic motion design commonly seen in the prior art, such as disposing an elastic sheet between the probe 30 and the conductive member 32. In other words, all designs in which the probe could move elastically relative to the panel imitation member between the initial position and the triggering position would fall within the scope of the present invention.

Figure 4:
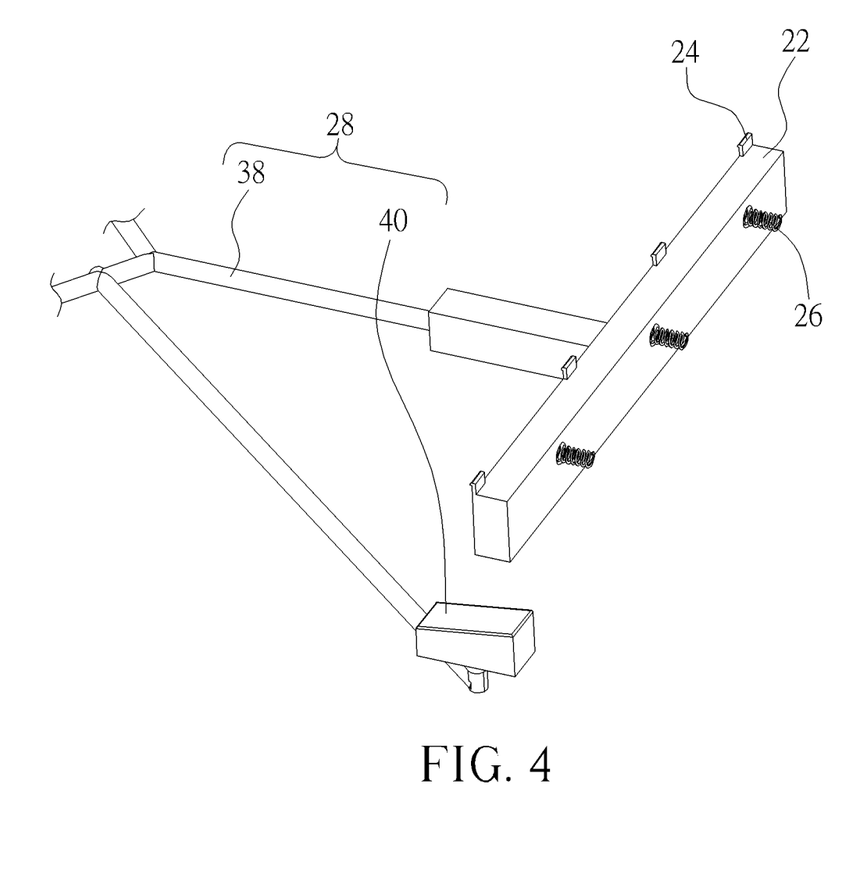
FIG. 4 is a partial enlarged diagram of a sliding bock, an elastic member, a hook, and a driving device in FIG. 2.

Furthermore, the testing tool 10 could preferably adopt the design in which a hook could be engaged with or separate from the test panel cover 12 for detachably positioning the test panel cover 12 on the tool body 14, but not limited thereto, meaning that the testing tool 10 could adopt other positioning design (e.g. a hole-shaft positioning design). In this embodiment, the testing tool 10 could include four sliding blocks 22, and each sliding block 22 could have at least four hooks 24 and three elastic members 26 disposed thereon (as shown in FIG. 2 and FIG. 4). To be noted, number of the sliding blocks 22, the hooks 24, and the elastic member 26 could vary with the practical application of the testing tool 10. Furthermore, the driving device 28 is disposed in the tool body 14 and connected to each sliding block 22. To be more specific, in this embodiment, the driving device 28 could preferably adopt a pneumatic driving design. As shown in FIG. 2 and FIG. 4, the driving device 28 could include at least one air pressure rod 38 (four shown in FIG. 2, but not limited thereto) and a switch 40. Each air pressure rod 38 is connected to the corresponding sliding block 22. The switch 40 is disposed on the air pressure rods 38 for controlling each air pressure rod 38 to drive the corresponding sliding block 22 to a position where the corresponding hook 24 is separate from the test panel cover 12.

Figure 5:
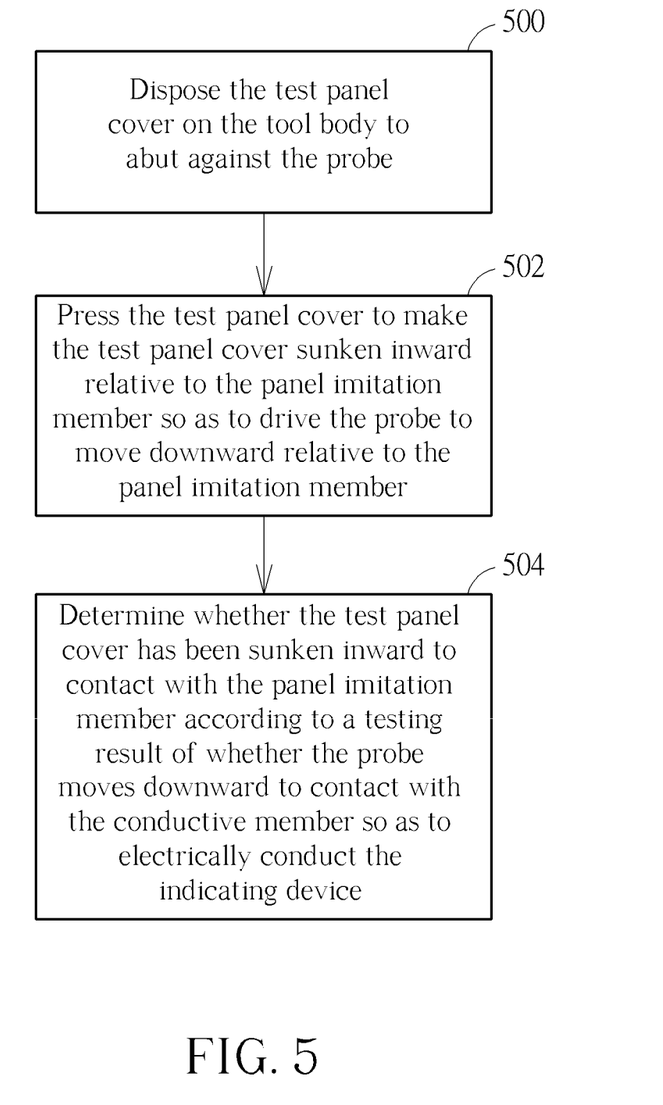
FIG. 5 is a flowchart of a testing method of utilizing the testing tool in FIG. 1 to test the test panel cover.
Figure 6:
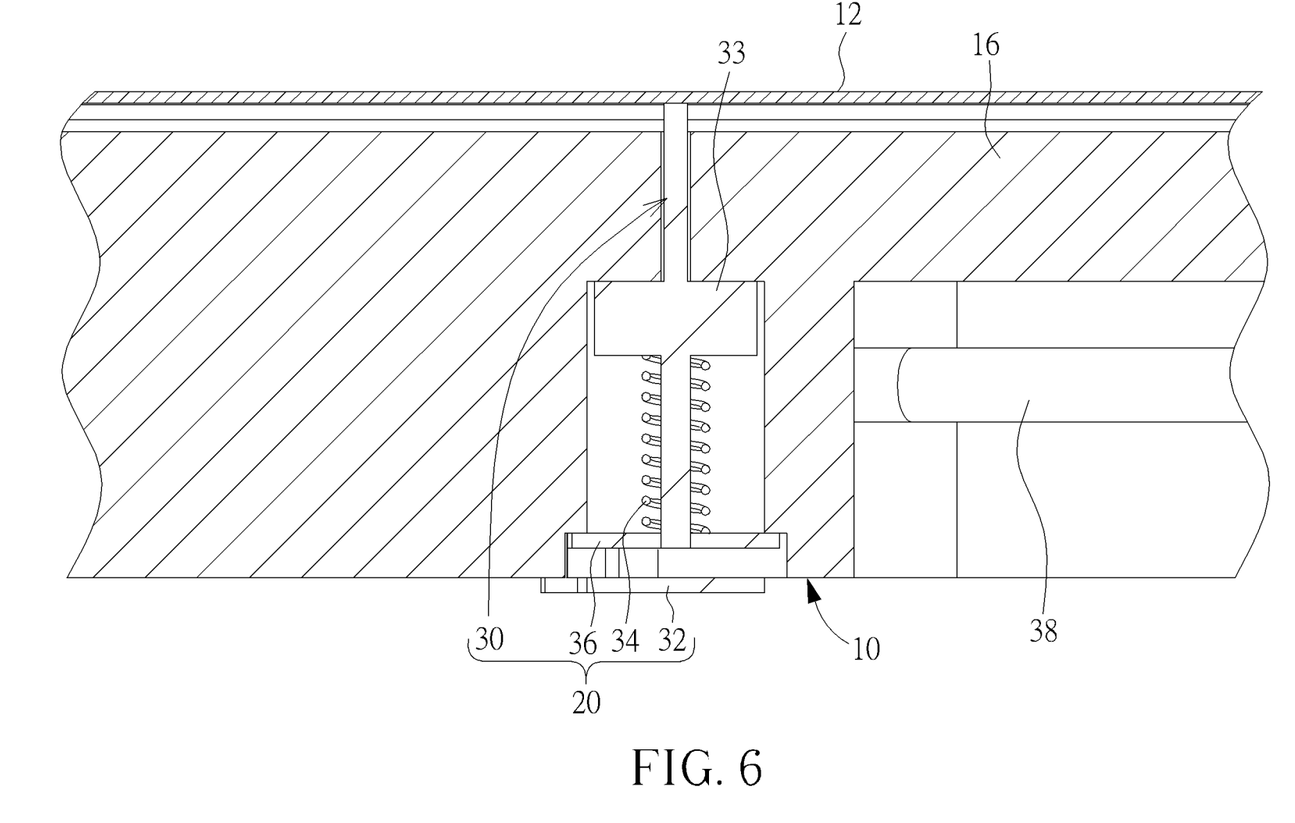
FIG. 6 is a partial sectional diagram of the testing tool in FIG. 1 along a sectional line A-A'.
Figure 7:
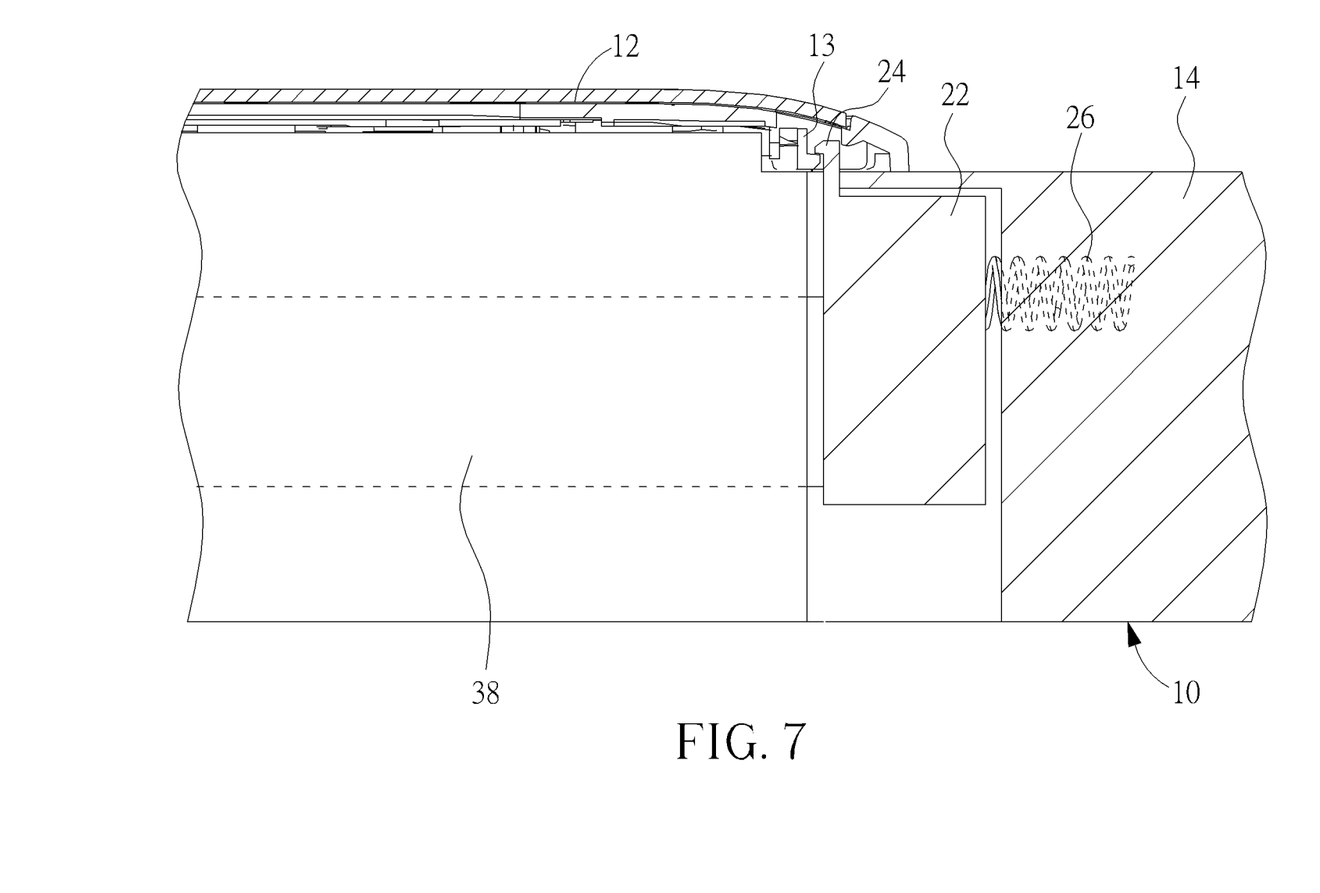
FIG. 7 is a partial sectional diagram of the testing tool in FIG. 1 along a sectional line B-B'.
Figure 8:
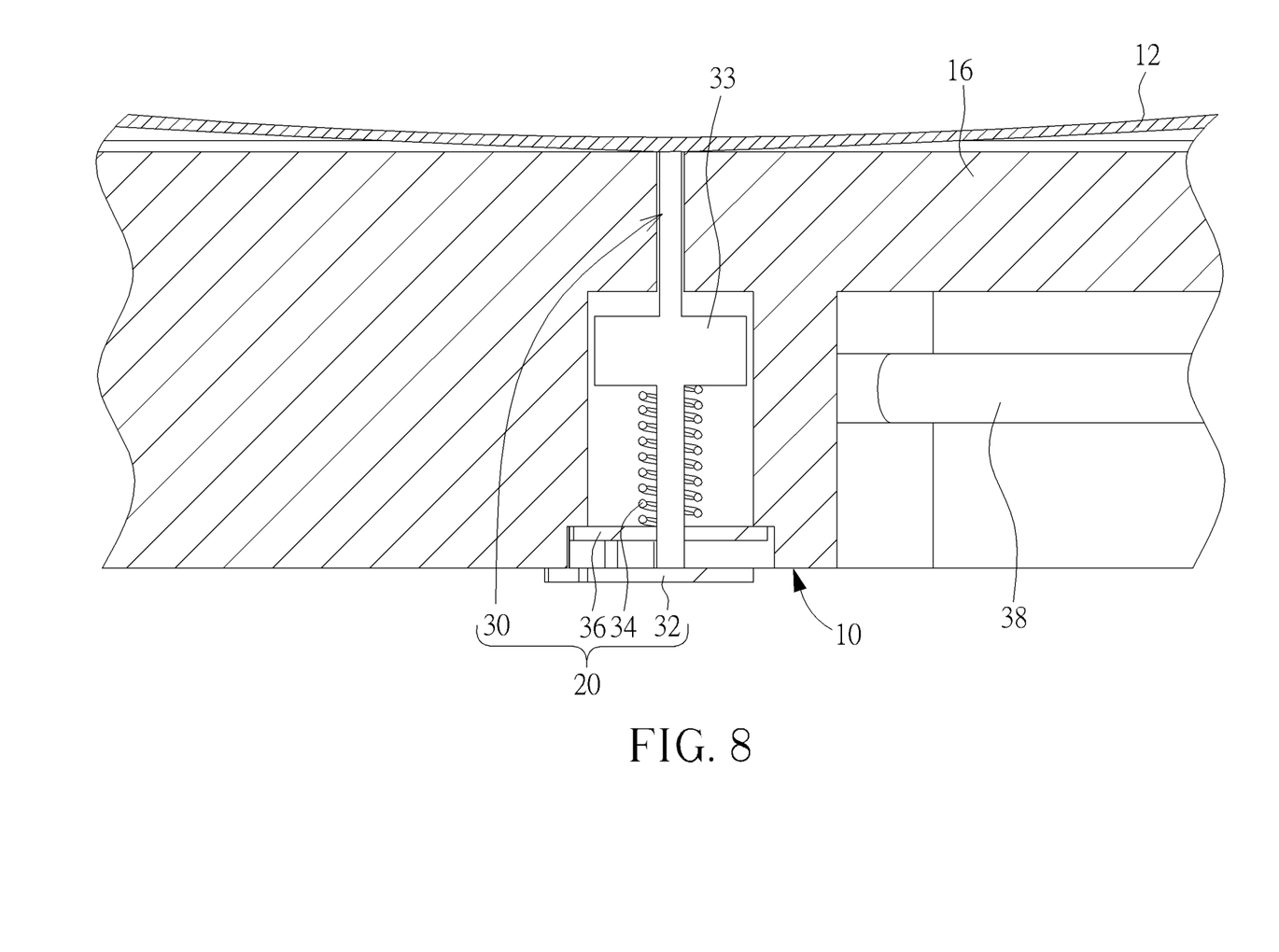
FIG. 8 is a partial sectional diagram of a probe in FIG. 6 moving to a triggering position.
Figure 9:
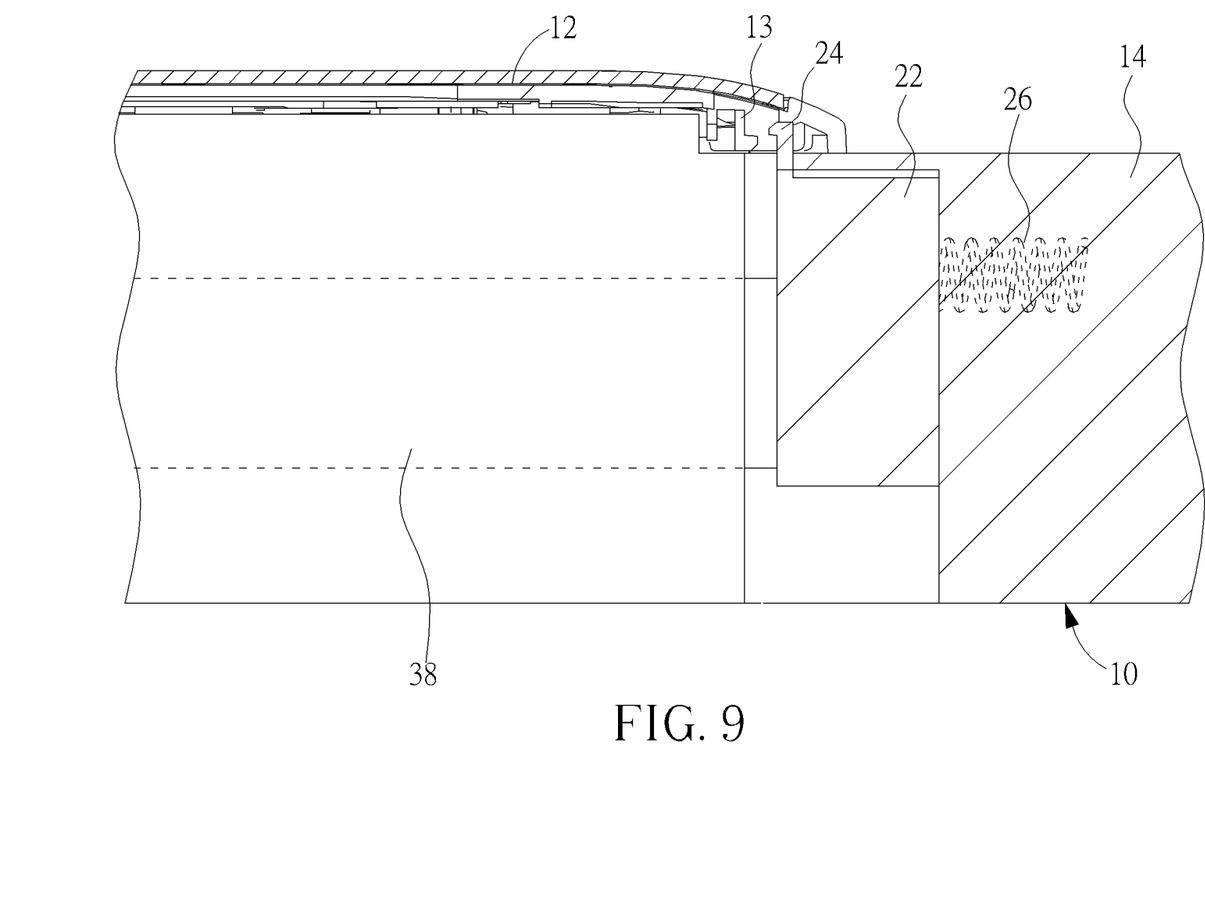
FIG. 9 is a partial sectional diagram of the sliding block in FIG. 7 moving to a releasing position.

More detailed description for the operation of the testing tool 10 is provided as follows. Please refer to FIG. 5, FIG. 6, FIG. 7, FIG. 8, and FIG. 9. FIG. 5 is a flowchart of a testing method of utilizing the testing tool 10 in FIG. 1 to test the test panel cover 12. FIG. 6 is a partial sectional diagram of the testing tool 10 in FIG. 1 along a sectional line A-A'. FIG. 7 is a partial sectional diagram of the testing tool 10 in FIG. 1 along a sectional line B-B'. FIG. 8 is a partial sectional diagram of the probe 30 in FIG. 6 moving to a triggering position. FIG. 9 is a partial sectional diagram of the sliding block 22 in FIG. 7 moving to a releasing position. The testing method includes the following steps.

Step 500: Dispose the test panel cover 12 on the tool body 14 to abut against the probe 30;

Step 502: Press the test panel cover 12 to make the test panel cover 12 sunken inward relative to the panel imitation member 16 so as to drive the probe 30 to move downward relative to the panel imitation member 16;

Step 504: Determine whether the test panel cover 12 has been sunken inward to contact with the panel imitation member 16 according to a testing result of whether the probe 30 moves downward to contact with the conductive member 32 so as to electrically conduct the indicating device 18.

In Step 500, the user could dispose the test panel cover 12 on the tool body 14. To be more specific, the user could directly place the test panel cover 12 on the tool body 14 and then press the periphery of the test panel cover 12 to make each hook 24 engaged with a corresponding engaging slot 13 formed on the test panel cover 12 (as shown in FIG. 7). The engaging slot 13 could be an engaging structure formed on the test panel cover 12 for assembling with a panel bezel or other engaging structure capable of assembling with the hook 24. In such a manner, the test panel cover 12 could be positioned on the tool body 14 steadily. At this time, as shown in FIG. 6, the test panel cover 12 abuts against the probe 30.

After disposing the test panel cover 12 on the tool body 14, the user could press the test panel cover 12 (Step 502). At this time, a residual stress formed at a position (e.g. a position where a trademark is formed) on the test panel cover 12 where a surface treatment (e.g. a surface milling process) is performed could cause the test panel cover 12 to be sunken inward and then generate sound like a drumbeat. Subsequently, according to a testing result of whether the probe 30 moves downward to contact with the conductive member 32 so as to electrically conduct the indicating device 18, the user could determine whether the test panel cover 12 has been sunken inward to contact with the panel imitation member 16.

For example, if there is an excessive residual stress formed in the test panel cover 12 so that the test panel cover 12 could be sunken inward to contact with the panel imitation member 16, the test panel cover 12 could drive the probe 30 to move downward relative to the panel imitation member 16 from the initial position as shown in FIG. 6 to the triggering position as shown in FIG. 8 to contact with the conductive member 32. As a result, the probe 30 and the conductive member 32 could electrically conduct the indicating device 18 to cause the indicating device 18 to emit light, so that the user could determine that the test panel cover 12 is sunken inward by the residual stress to contact with the panel imitation member 16 when being pressed. Thus, the user could accurately know that the test panel cover 12 has a risk to damage the liquid crystal panel and then determine whether to perform a structural enhancement process (e.g. a structural strengthening process or a stress relief process) on the test panel cover 12 according to the aforesaid testing result. In such a manner, the present invention could efficiently prevent the aforesaid prior art problem (e.g. moire or hotspot) caused by the panel cover with an excessive residual stress damaging the liquid crystal panel, so as to improve the display quality of the liquid crystal panel.

On the other hand, if the residual stress formed in the test panel cover 12 could not cause the test panel cover 12 to drive the probe 30 to the triggering position as shown in FIG. 8, the indicating device 18 is in the open circuit state since the probe 30 has not contacted with the conductive member 32 yet. Accordingly, the indicating device 18 is unable to emit light, so as to let the user accurately know that the residual stress could not cause the test panel cover 12 to damage the liquid crystal panel. That is, even if inward deformation of the test panel cover 12 occurs due to the residual stress, the test panel cover 12 would not be sunken inward to collide with the panel imitation member 16. Thus, the user could determine whether to directly utilize the test panel cover 12 to perform the following assembly process of the portable electronic apparatus according to the aforesaid testing result.

After the aforesaid testing steps are completed, the user could turn on the switch 20 to activate the air pressure rod 38 so that the air pressure rod 38 could drive the sliding block 22 to overcome the elastic force provided by the elastic member 26 and then move from the engaging position as shown in FIG. 7 to the releasing position as shown in FIG. 9. At this time, since the engaging slot 13 of the test panel cover 12 is no longer engaged with the hook 24, the user could detach the test panel cover 12 from the tool body 14.

To be noted, after the user detaches the test panel cover 12 from the tool body 14 and then turns off the switch 13 for controlling the air pressure rod 38 not to drive the sliding block 22, elastic force provided by the elastic member 26 could accordingly drive the sliding block 22 from the releasing position as shown in FIG. 9 back to the engaging position as shown in FIG. 7. At the same time, elastic force provided by the elastic member 34 could drive the probe 30 from the triggering position as shown in FIG. 8 to the initial position as shown in FIG. 6 where the probe 30 extends out from the panel imitation member 16. In such a manner, the user could continue to test the next test panel cover. Furthermore, besides the pneumatic driving mechanism mentioned in the aforesaid embodiment, the driving device 28 could also utilize other conventional driving mechanism. For example, in other embodiment, the driving device 28 could utilize a mechanical driving mechanism (e.g. a gear driving mechanism) or a hydraulic driving mechanism to drive each sliding block 22 to the releasing position as shown in FIG. 9. As for description for the related driving principles and designs, it is commonly seen in the prior art and therefore omitted herein.

In summary, the testing tool provided by the present invention adopts the testing method of determining whether the test panel cover is sunken inward to drive the probe to electrically conduct the indicating device, for helping the user determine whether the test panel cover has a risk to damage the liquid crystal panel. In such a manner, via the aforesaid testing method, the user could accurately determine whether to perform a structural enhancement (e.g. a structural strengthening process or a stress relief process) process on the test panel cover or directly assemble the test panel cover with the liquid crystal panel. Thus, the present invention could efficiently prevent the aforesaid prior art problem (e.g. moire or hotspot) caused by the panel cover with an excessive residual stress damaging the liquid crystal panel, so as to improve the display quality of the liquid crystal panel.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A testing tool for testing inward deformation of a test panel cover, the testing tool comprising:
   a tool body, the test panel cover being detachably disposed on the tool body;
   a panel imitation member disposed on the tool body, the panel imitation member being contained between the tool body and the test panel cover when the test panel cover is disposed on the tool body;
   an indicating device disposed on the tool body; and
   a probe device disposed in the panel imitation member, the probe device comprising:
      a probe elastically disposed through the panel imitation member between an initial position and a triggering position and coupled to the indicating device, the probe extending out from the panel imitation member to abut against the test panel cover when the probe is located at the initial position; and
      a conductive member disposed under the probe and coupled to the indicating device, the probe contacting with the conductive member to electrically conduct the indicating device when the test panel cover is sunken inward to contact with the panel imitation member so as to drive the probe to the triggering position.

2. The testing tool of claim 1, wherein a limiting block protrudes outwardly from the probe, and the probe device further comprises:
   a first elastic member mounted on the probe and disposed between the limiting block and the conductive member for providing elastic force to drive the probe to the initial position.

3. The testing tool of claim 2, wherein the probe device further comprises:
   an insulation member mounted on the probe, two ends of the first elastic member abutting against the limiting block and the insulation member.

4. The testing tool of claim 3 further comprising:
   at least one sliding block movably disposed in the tool body between a releasing position and an engaging position; and
   at least one hook disposed on the at least one sliding block for hooking the test panel cover to position the test panel cover on the tool body when the test panel cover is disposed on the tool body and the at least one sliding block moves to the engaging position, the at least one hook being further used for being separate from the test panel cover when the at least one sliding block moves to the releasing position.

5. The testing tool of claim 4, wherein the test panel cover has at least one engaging slot, the at least one hook is disposed on the at least one sliding block corresponding to the at least one engaging slot, the at least one hook is engaged with the at least one engaging slot to position the test panel cover on the tool body when the test panel cover is disposed on the tool body and the at least one sliding block moves to the engaging position, and the at least one hook is separate from the at least one engaging slot when the at least one sliding block moves to the releasing position.

6. The testing tool of claim 5 further comprising:
   at least one second elastic member disposed between the at least one sliding block and the tool body for providing elastic force to drive the at least one sliding block to the engaging position.

7. The testing tool of claim 6 further comprising:
   a driving device disposed in the tool body and connected to the at least one sliding block for driving the at least one sliding block to the releasing position.

8. The testing tool of claim 7, wherein the driving device comprises:
   at least one air pressure rod connected to the at least one sliding block; and
   a switch disposed on the at least one air pressure rod for controlling the at least one air pressure rod to drive the at least one sliding block to the releasing position.

9. The testing tool of claim 1 further comprising:
   at least one sliding block movably disposed in the tool body between a releasing position and an engaging position; and
   at least one hook disposed on the at least one sliding block for hooking the test panel cover to position the test panel cover on the tool body when the test panel cover is disposed on the tool body and the at least one sliding block moves to the engaging position, the at least one hook being further used for being separate from the test panel cover when the at least one sliding block moves to the releasing position.

10. The testing tool of claim 9, wherein the test panel cover has at least one engaging slot, the at least one hook is disposed on the at least one sliding block corresponding to the at least one engaging slot, the at least one hook is engaged with the at least one engaging slot to position the test panel cover on the tool body when the test panel cover is disposed on the tool body and the at least one sliding block moves to the engaging position, and the at least one hook is separate from the at least one engaging slot when the at least one sliding block moves to the releasing position.

11. The testing tool of claim 9 further comprising:
at least one second elastic member disposed between the at least one sliding block and the tool body for providing elastic force to drive the at least one sliding block to the engaging position.

12. The testing tool of claim 9 further comprising:
a driving device disposed in the tool body and connected to the at least one sliding block for driving the at least one sliding block to the releasing position.

13. The testing tool of claim 12, wherein the driving device comprises:
at least one air pressure rod connected to the at least one sliding block; and
a switch disposed on the at least one air pressure rod for controlling the at least one air pressure rod to drive the at least one sliding block to the releasing position.

14. The testing tool of claim 1, wherein the indicating device is an indicating lamp, and the indicating device emits light to indicate that the test panel cover has been sunken inward to contact with the panel imitation member.

15. A testing method for utilizing a testing tool to test inward deformation of a test panel cover, the testing tool comprising a tool body, a panel imitation member, an indicating device, and a probe device, the panel imitation member being disposed on the tool body, the probe device comprising a probe and a conductive member, the probe being movable up and down relative to the panel imitation member and coupled to the indicating device, the conductive member being coupled to the indicating device, the testing method comprising:
disposing the test panel cover on the tool body to abut against the probe;
pressing the test panel cover to make the test panel cover sunken inward relative to the panel imitation member so as to drive the probe to move downward relative to the panel imitation member; and
determining whether the test panel cover has been sunken inward to contact with the panel imitation member according to a testing result of whether the probe moves downward to contact with the conductive member so as to electrically conduct the indicating device.

16. The testing method of claim 15, wherein the testing tool further comprises at least one hook, and the step of disposing the test panel cover on the tool body to abut against the probe comprises:
utilizing the at least one hook to be detachably engaged with the test panel cover for positioning the test panel cover on the tool body.

17. The testing method of claim 16, wherein the step of utilizing the at least one hook to be detachably engaged with the test panel cover for positioning the test panel cover on the tool body comprises:
pneumatically driving the at least one hook to be separate from the test panel cover.

18. The testing method of claim 15, wherein the indicating device is an indicating lamp, and the indicating device emits light to indicate that the test panel cover has been sunken inward to contact with the panel imitation member.

* * * * *